(12) United States Patent
Tsutsumi et al.

(10) Patent No.: US 9,161,719 B2
(45) Date of Patent: Oct. 20, 2015

(54) SLEEP EVALUATION DEVICE

(71) Applicant: OMRON HEALTHCARE CO., LTD., Muko-shi, Kyoto (JP)

(72) Inventors: Masakazu Tsutsumi, Kyoto (JP); Hiroshi Harada, Kyoto (JP); Hirotaka Hara, Yamaguchi (JP); Hidetaka Togo, Kyoto (JP)

(73) Assignee: Omron Healthcare Co., Ltd., Kyoto (JP)

( * ) Notice: Subject to any disclaimer, the term of this patent is extended or adjusted under 35 U.S.C. 154(b) by 0 days.

(21) Appl. No.: 14/360,382

(22) PCT Filed: Oct. 17, 2012

(86) PCT No.: PCT/JP2012/076812
§ 371 (c)(1),
(2) Date: May 23, 2014

(87) PCT Pub. No.: WO2013/077118
PCT Pub. Date: May 30, 2013

(65) Prior Publication Data
US 2014/0323919 A1 Oct. 30, 2014

(30) Foreign Application Priority Data
Nov. 24, 2011 (JP) ................... 2011-256414

(51) Int. Cl.
*A61B 5/00* (2006.01)
*A61B 7/00* (2006.01)
(Continued)

(52) U.S. Cl.
CPC .............. *A61B 5/4818* (2013.01); *A61B 5/0826* (2013.01); *A61B 5/11* (2013.01); *A61B 5/4806* (2013.01); *A61B 7/003* (2013.01)

(58) Field of Classification Search
CPC .. A61B 5/4818; A61B 5/0826; A61B 5/4806; A61B 5/4809; A61B 5/4815; A61B 7/003; A61B 5/11
USPC ........................................................ 600/586
See application file for complete search history.

(56) References Cited

U.S. PATENT DOCUMENTS

| | | | | |
|---|---|---|---|---|
| 5,203,343 | A * | 4/1993 | Axe .......................... | A61F 5/56 128/848 |
| 2006/0212273 | A1* | 9/2006 | Krausman .............. | A61B 5/087 702/189 |

(Continued)

FOREIGN PATENT DOCUMENTS

| CN | 101933798 A | 1/2011 |
|---|---|---|
| CN | 102138796 A | 8/2011 |

(Continued)

OTHER PUBLICATIONS

Cavusoglu et al. "An efficient method for snore/nonsnore classification of sleep sounds" Physiol. Meas. 28 (2007) 841-853.*

(Continued)

*Primary Examiner* — Michael C Stout
(74) *Attorney, Agent, or Firm* — Keating & Bennett, LLP

(57) ABSTRACT

A sleep evaluation device includes an obtainment unit configured to obtain audio and a determination unit configured to determine a snoring level in the audio obtained by the obtainment unit based on an amount of time for which the audio occurred. The determination unit is configured to determine a snoring level based on a ratio of a cumulative time in which the obtainment unit obtains the audio to a number of times the audio is obtained by the obtainment unit.

5 Claims, 12 Drawing Sheets

(51) Int. Cl.
*A61B 5/08* (2006.01)
*A61B 5/11* (2006.01)

(56) References Cited

U.S. PATENT DOCUMENTS

| | | | |
|---|---|---|---|
| 2009/0234241 A1* | 9/2009 | Ota | A61B 5/0002 600/529 |
| 2011/0224510 A1* | 9/2011 | Oakhill | A61B 5/11 600/301 |
| 2012/0071741 A1* | 3/2012 | Moussavi | A61B 5/4818 600/340 |
| 2012/0184825 A1* | 7/2012 | Ben David | 600/301 |
| 2013/0144190 A1* | 6/2013 | Bruce | A61B 5/4818 600/586 |
| 2013/0204314 A1* | 8/2013 | Miller et al. | 607/42 |

FOREIGN PATENT DOCUMENTS

| | | |
|---|---|---|
| JP | 2006-014813 A | 1/2006 |
| JP | 2006-167427 A | 6/2006 |
| JP | 2009-539499 A | 11/2009 |
| WO | 2010/044162 A1 | 4/2010 |

OTHER PUBLICATIONS

Official Communication issued in International Patent Application No. PCT/JP2012/076812, mailed on Jan. 15, 2013.

Official Communication issued in corresponding Chinese Patent Application No. 201280057500.8, mailed on May 11, 2015.

* cited by examiner (SOURCE: FUMIHIKO YASUMA, "SLEEP APNEA SYNDROME")

SLEEP EVALUATION DEVICE

BACKGROUND OF THE INVENTION

1. Field of the Invention

The present invention relates to sleep evaluation devices, and particularly relates to sleep evaluation devices that evaluate the state of a measurement subject's sleep in a non-invasive manner.

2. Description of the Related Art

Various conventional techniques have been disclosed with respect to devices for evaluating sleep.

For example, JP 2006-014813A discloses a technique, aimed at identifying symptoms of insomnia, that determines a sleep state from information such as breathing, body movement, heartbeats, and so on obtained from a mat-shaped pressure sensor, and creates a chronological sleep log.

In addition to insomnia, snoring is another sleep-related condition for which there is demand for relief. Snoring is problematic not only because of the discomfort it causes people sleeping in the same room, but also because it is said to involve more serious problems such as Sleep Apnea Syndrome.

With respect to the detection of snoring, JP 2006-167427A discloses a technique in which respiratory sounds are obtained during sleep, the obtained respiratory sounds are divided into a plurality of frequency blocks and determination values are detected for physical amounts in each block, and the person's respiratory sounds during sleep are identified as at least one of quiet breathing, snoring, and loud snoring based on the determination values.

However, performing analysis and so on on frequency blocks of obtained sound as disclosed in JP 2006-167427A requires an advanced level of processing, and thus comparatively high-performance information processing devices are required for devices that evaluate sleep in this manner. Accordingly, there is a problem in that there is an increase in the cost of such devices.

SUMMARY OF THE INVENTION

Preferred embodiments of the present invention provide a sleep evaluation device capable of detecting snoring during sleep while also realizing a comparatively low device cost.

A sleep evaluation device according to a preferred embodiment of the present invention includes an obtainment unit configured to obtain audio and a determination unit configured to determine a snoring level in the audio obtained by the obtainment unit based on an amount of time during which the audio occurred, where the determination unit is configured to determine the snoring level based on a ratio of a cumulative time in which the obtainment unit obtains the audio to a number of times the audio is obtained by the obtainment unit.

Preferably, the determination unit is configured to determine the snoring level in each of predetermined periods, and to determine that snoring has not occurred if the cumulative time in which the audio is obtained in the predetermined period is longer than a first time or is shorter than a second time that is shorter than the first time.

Preferably, the determination unit is configured to determine the snoring level in each of predetermined periods, and to determine that snoring has not occurred if a number of times audio is obtained in the predetermined period is greater than or equal to a first number of times or less than a second number of times that is less than the first number of times.

Preferably, the sleep evaluation device further includes a detector configured to detect body movement in a measurement subject, and a display controller configured and programmed to cause the body movement detected by the detector and change over time in the snoring level determined by the determination unit to be displayed by a display device.

A sleep evaluation device according to another preferred embodiment of the present invention includes an obtainment unit configured to obtain audio, and a determination unit configured to determine whether or not sleep apnea syndrome snoring has occurred based on a length of a period in which audio continuously occurs and a length of a period in which no audio occurs continuously in the audio obtained by the obtainment unit.

According to various preferred embodiments of the present invention, a snoring level is determined based on an amount of time in which audio has occurred. As a result, the sleep evaluation device is not required to perform advanced processing, and thus a comparatively low cost is achieved.

Furthermore, according to various preferred embodiments of the present invention, whether or not sleep apnea syndrome snoring has occurred is determined based on the length of a period in which audio continuously occurs and the length of a period in which no audio occurs continuously. As a result, the sleep evaluation device is not required to perform advanced processing, and thus a comparatively low cost is achieved.

The above and other elements, features, steps, characteristics and advantages of the present invention will become more apparent from the following detailed description of the preferred embodiments with reference to the attached drawings.

DETAILED DESCRIPTION OF THE PREFERRED EMBODIMENTS

Figure 1:
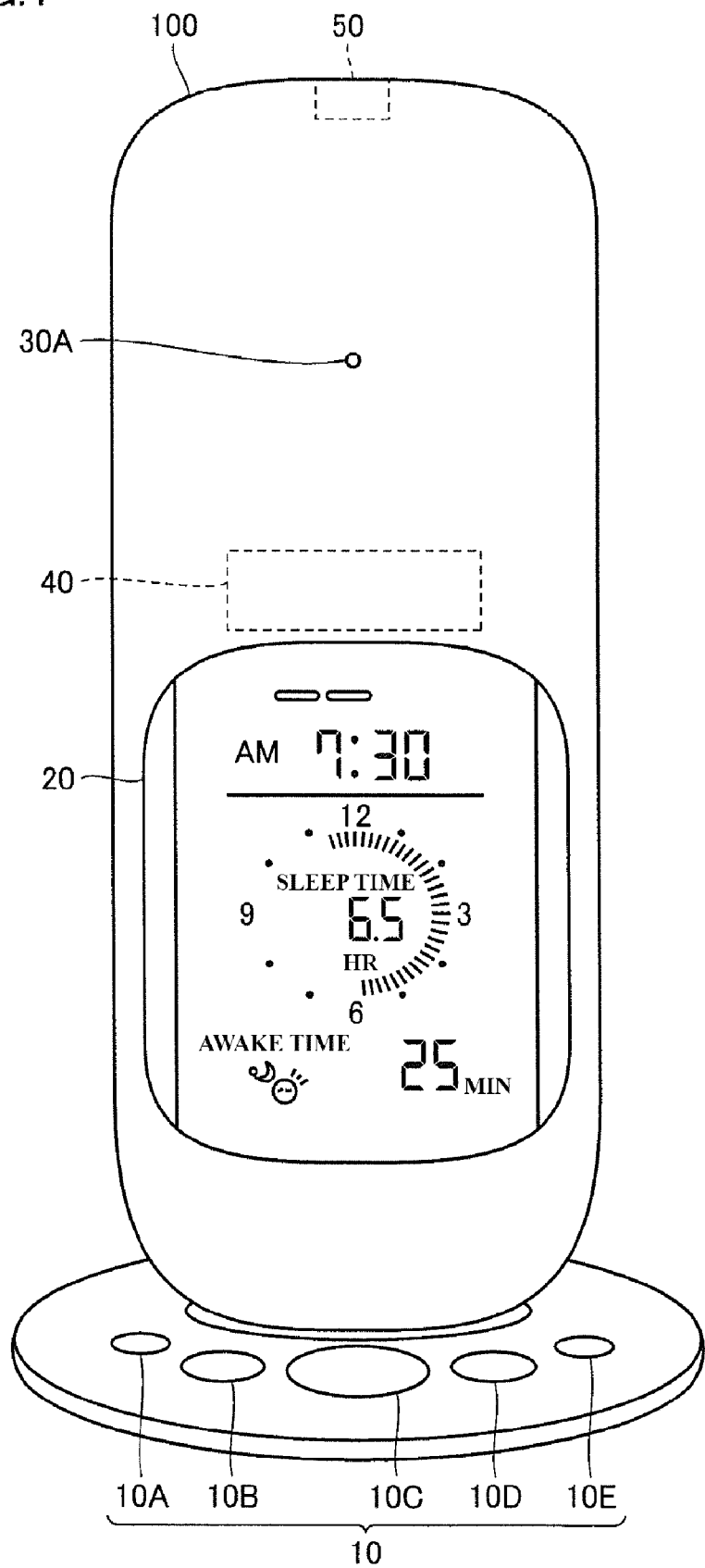
FIG. 1 is a diagram illustrating a specific example of the external appearance of a sleep evaluation device according to a preferred embodiment of the present invention.

Hereinafter, preferred embodiments of the present invention will be described with reference to the drawings. In the following descriptions, identical reference numerals are assigned to identical components and constituent elements. The names and functions thereof are also the same.

Figure 2:
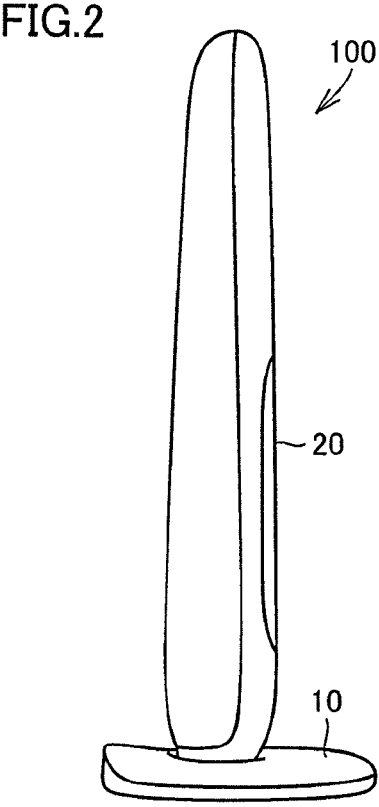
FIG. 2 is a schematic diagram illustrating the sleep evaluation device from the side.

FIG. 1 is a diagram illustrating a specific example of the external appearance of a sleep evaluation device 100 according to the present preferred embodiment. FIG. 2, meanwhile, is a schematic diagram illustrating the sleep evaluation device 100 from the side, whereas FIG. 3 is a schematic diagram illustrating the exterior of the sleep evaluation device 100 from above at an angle.

Figure 3:
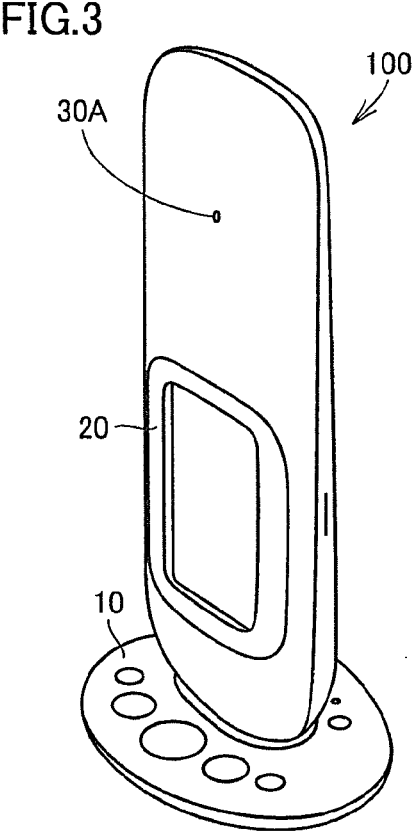
FIG. 3 is a schematic diagram illustrating the exterior of the sleep evaluation device from above at an angle.

As shown in FIGS. 1 to 3, the sleep evaluation device 100 has an external form in which, for example, a box member having a rectangular or substantially rectangular shape or a vertically-elongated shape with rounded corners is attached to a platform in an upright state.

As shown in FIG. 1, a button group 10 used for operations is disposed in a surface of the platform. The button group 10 includes buttons 10A to 10E. Meanwhile, the box member includes a microphone (a microphone 30, described later), a control unit 40, and a communication unit 50. A display unit 20 is provided in a surface of the box member that is set upright on the platform, and a microphone port 30A configured to allow sound to enter the microphone is provided in the surface of the box member as well.

The communication unit 50 communicates with other devices wirelessly or over wires. The communication unit 50 is provided, for example, toward the end of the box member on the opposite side as the platform. Using the communication unit 50, the sleep evaluation device 100 can be connected to a display device such as a personal computer ("PC" hereinafter) or a mobile telephone unit (not shown) and output display data to that display device.

Figure 4:
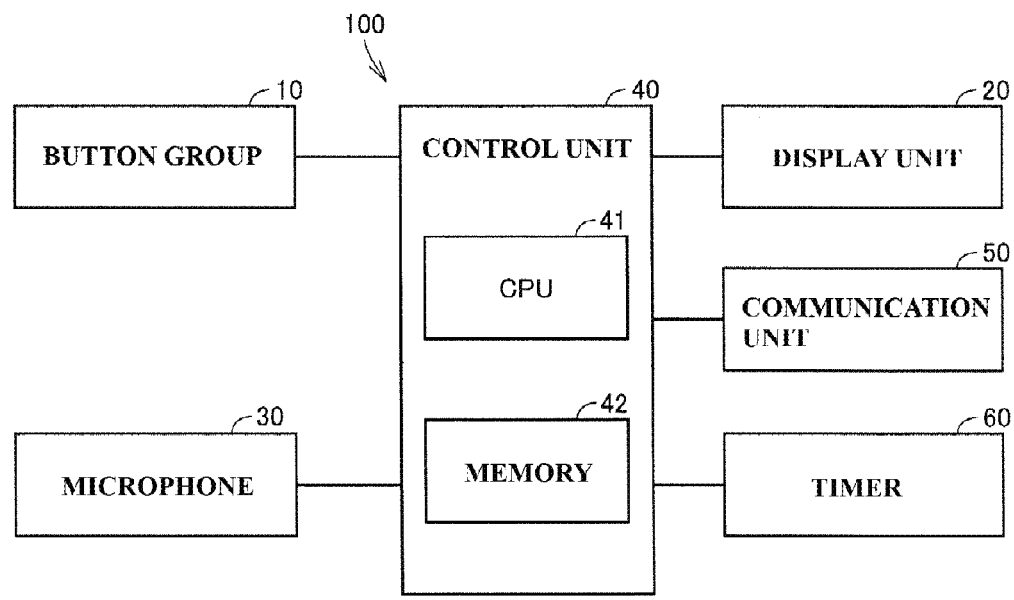
FIG. 4 is a block diagram illustrating a specific example of the hardware configuration of the sleep evaluation device.

FIG. 4 is a block diagram illustrating a specific example of the hardware configuration of the sleep evaluation device 100.

As shown in FIG. 4, the button group 10, the microphone 30, the display unit 20, and the communication unit 50 are all connected to the control unit 40. The microphone 30 according to the present preferred embodiment configures a body movement sensor. Note that a Doppler sensor, an ultrasound sensor, or the like may be used as the body movement sensor. Furthermore, a camera may be used as the body movement sensor by detecting body movement in a measurement subject through image analysis performed by the control unit 40.

Each of the buttons 10A to 10E in the button group 10 (see FIG. 1) output operation signals to the control unit 40 indicating that the corresponding button has been manipulated.

The control unit 40 includes a CPU (Central Processing Unit) 41 configured and programmed to perform overall control and a memory 42 configured to store programs and the like executed by the CPU 41.

The control unit 40 is configured and programmed to detect a snoring level by the CPU 41 executing a display program stored in the memory 42 and executing computations using inputted operation signals and sensor signals. The control unit 40 furthermore is configured and programmed to detect snoring resulting from SAS (Sleep Apnea Syndrome) (called simply "SAS snoring" as appropriate hereinafter), snoring resulting from OSAS (Obstructive Sleep Apnea Syndrome) (called simply "OSAS snoring" as appropriate hereinafter), and so on.

A process to output the level and so on mentioned above includes generating display data and carrying out display control so that the display unit 20 displays a screen based on the display data. Note that this process may also include communication control to send the display data to an external display device via the communication unit 50.

The communication unit 50 may communicate directly with the display device through wireless communication over, for example, infrared or Bluetooth® connections, or may be configured to connect to the Internet and may communicate with the display device over the Internet.

Furthermore, the communication unit 50 may function as a wireless LAN (Local Area Network) server, and may send the display data (which will be described later) written in a markup language such as HTML (Hyper Text Markup Language) to a display device accessed over a wireless LAN connection, for example.

Figure 5:
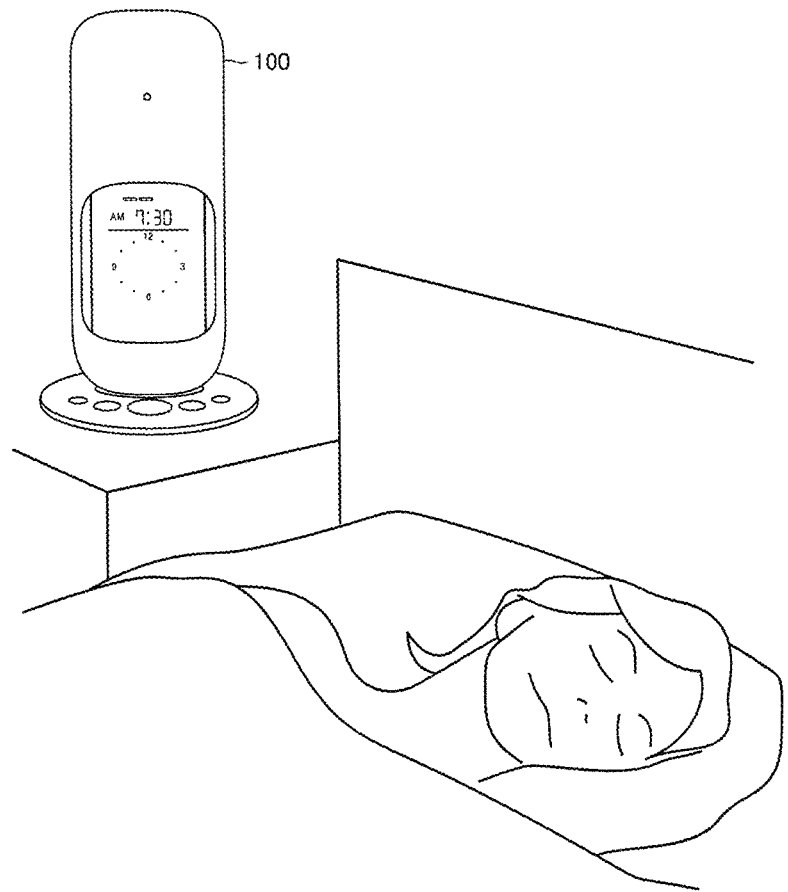
FIG. 5 is a diagram illustrating an example of the sleep evaluation device in use.

FIG. 5 is a diagram illustrating an example of the sleep evaluation device 100 in use.

As shown in FIG. 5, the sleep evaluation device 100 is placed nearby the measurement subject and detects audio from the vicinity of the measurement subject using the microphone 30, which serves as an audio sensor. An audio signal is outputted to the control unit 40 as a sensor signal.

The control unit 40 detects "snoring" from the measurement subject using the audio signal, and determines a state of the snoring based on a result of the detection.

OSAS will be described next. OSAS refers to a situation where the muscles in the root of the tongue, the throat, and so on relax during sleep, causing the upper airway to gradually constrict and eventually become obstructed, which in turn leads to reduced breathing or apnea. OSAS is also considered a cause of cerebrovascular disease. Obesity, functional abnormalities in the upper airway muscles, and so on can be given as causes of OSAS.

Patients exhibiting OSAS symptoms repeat a cyclic sleep pattern during sleep, which will be described below. This sleep pattern is referred to as the "OSAS cycle". OSAS also produces a characteristic snore having a unique sound pressure. This snore will be referred to as "OSAS snoring" in the following descriptions. As opposed to normal snoring, which is regular and temporary, OSAS snoring is produced when the root of the tongue, the palate area, and so on vibrate due to constriction in the upper airway, and is thus irregular.

Figure 20:
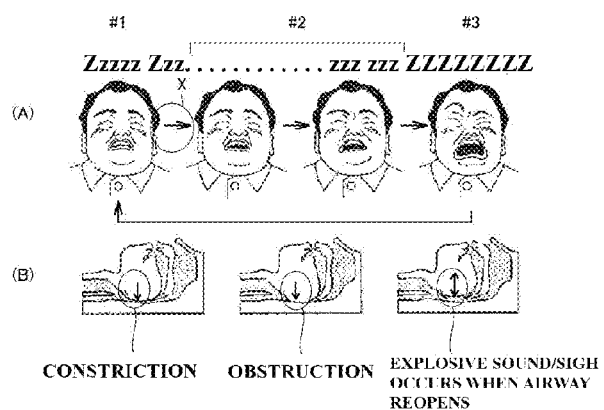
FIGS. 20A and 20B are diagrams illustrating the mechanics of an OSAS cycle.

FIGS. 20A and 20B are diagrams illustrating the mechanics of the OSAS cycle.

As shown in FIG. 20A, the OSAS cycle can be broadly divided into three stages.

In the first stage (#1), snoring gradually changes from normal snoring to OSAS snoring, which is a loud snore, as the upper airway constricts. In the second stage (#2), breathing becomes extremely shallow or ceases completely. Finally, in the third stage (#3), the body moves and an explosive sound or a sound resembling a heavy sigh is produced, resulting in a wakeful state.

During sleep, patients exhibiting OSAS symptoms cyclically repeat the OSAS cycle, which is this unique sleep pattern made up of the stages #1 to #3.

FIG. 20B is a diagram illustrating the state of the upper airway during the OSAS cycle.

As shown in FIG. 20B, in #1, the upper airway gradually constricts from a normal state. In #2, the upper airway constricts further until it is completely obstructed. In #3, the upper airway returns to the normal state. At that time, an explosive sound or a sound resembling a sigh is detected.

Figure 6:
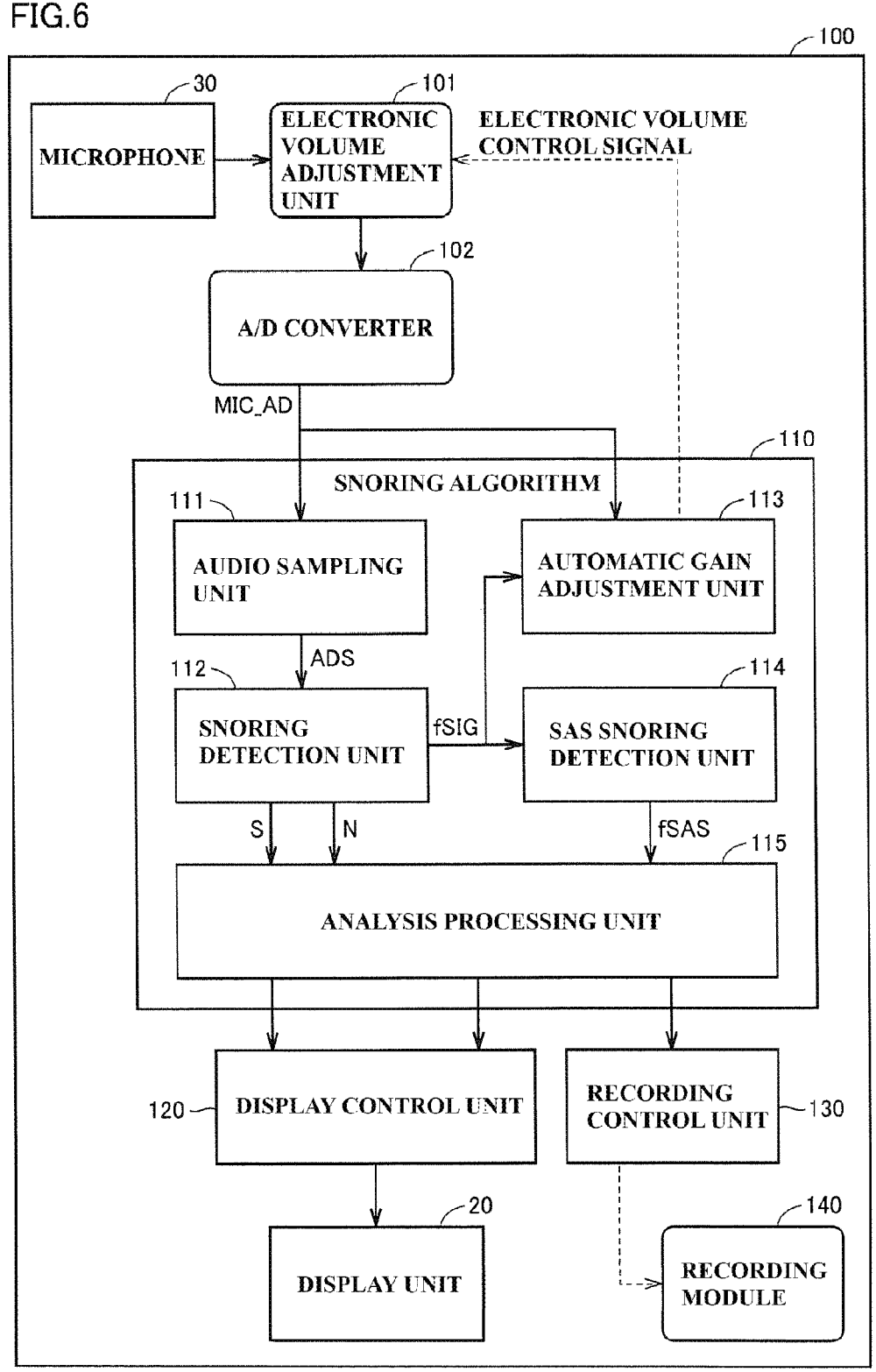
FIG. 6 is a diagram illustrating functional blocks of the sleep evaluation device.

FIG. 6 is a diagram illustrating functional blocks of the sleep evaluation device 100.

As shown in FIG. 6, in the sleep evaluation device 100, an audio signal inputted from the microphone 30 undergoes volume adjustment in an electronic volume adjustment unit 101, after which the signal is outputted to an A/D (analog/digital) converter 102. After being converted into a digital signal by the A/D converter 102, the audio signal is outputted to an audio sampling unit 111.

Note that the A/D converter 102 also outputs the post-conversion digital signal to an automatic gain adjustment unit 113. The automatic gain adjustment unit 113 generates a control signal for the electronic volume adjustment unit 101 based on the inputted audio signal and sends the control signal to the electronic volume adjustment unit 101. The electronic volume adjustment unit 101 then executes appropriate processes such as lowering the gain of the audio signal inputted from the microphone 30.

The audio sampling unit 111 executes a noise removal process on the digital signal outputted from the A/D converter 102 and outputs the resulting signal to a snoring detection unit 112.

The snoring detection unit 112 executes a snoring detection process based on details that will be described later with reference to FIG. 9 and so on, and outputs a result of the detection to an analysis processing unit 115.

The snoring detection unit 112 also outputs the signal from which noise has been removed, outputted from the audio sampling unit 111, to an SAS (Sleep Apnea Syndrome) snoring detection unit 114.

Based on the signal from which noise has been removed, outputted from the snoring detection unit 112, the SAS snoring detection unit 114 executes a snoring detection process in accordance with details that will be described later with reference to FIG. 15 and so on, and outputs a result of the detection to the analysis processing unit 115.

The snoring detection unit 112 sets a sounded segment determination threshold, which will be described later. Then, based on the stated sounded segment determination threshold, the audio sampling unit 111 detects the occurrence of snoring in the audio signal from which noise has been removed. Specifically, segments in which snoring occurs (sounded segments) and segments in which snoring does not occur (silent segments) are identified. A specific signal (fSIG) is sent to the automatic gain adjustment unit 113 during the sounded segments. Accordingly, the automatic gain adjustment unit 113 is configured to generate a control signal to adjust the gain of the digital signal outputted from the A/D converter 102 during a period when snoring occurs. Specifically, the snoring detection unit 112 outputs a signal fSIG=0 or fSIG=1, as will be described later. "0" indicates a silent segment, whereas "1" indicates a sounded segment. The automatic gain adjustment unit 113 then adjusts the gain in sounded segments, or in other words, in periods where fSIG=1.

Meanwhile, the snoring detection unit 112 also outputs the fSIG signal to the SAS snoring detection unit 114. The SAS snoring detection unit 114 executes processing based on the value of the fSIG signal.

Based on the detection outputs of the snoring detection unit 112 and the SAS snoring detection unit 114, the analysis processing unit 115 sends a control signal to a display control unit 120 to control the format in which the detection result is displayed in the display unit 20.

The sleep evaluation device 100 further includes a recording module 140 configured to record audio obtained by the microphone 30 and a recording control unit 130 configured and programmed to control operations of the recording module 140.

The analysis processing unit 115 outputs a trigger signal to cause the recording module 140 to start recording operations to the recording control unit 130 at a timing based on the detection result outputted from the SAS snoring detection unit 114.

With the sleep evaluation device 100, a snoring algorithm 110 is configured by the audio sampling unit 111, the snoring detection unit 112, the automatic gain adjustment unit 113, the SAS snoring detection unit 114, and the analysis processing unit 115. The snoring algorithm 110, the electronic volume adjustment unit 101, the A/D converter 102, the display control unit 120, and the recording control unit 130 are realized by the control unit 40. The control unit 40 includes hardware resources that configure these units. The snoring algorithm 110, the display control unit 120, and/or the recording control unit 130 in particular may be realized by the CPU 41 executing a program stored in the memory 42 (or a removable storage medium inserted into the sleep evaluation device 100). The recording module 140 also records audio by the CPU 41 executing a program stored in the memory 42 or the like. The audio is then stored in the memory 42 (or the removable storage medium inserted into the sleep evaluation device 100).

Media that store programs in a non-volatile or non-transitory manner, such as the following, can be given as examples of such a storage medium: CD-ROMs (Compact Disk-Read Only Memory), DVD-ROMs (Digital Versatile Disk-Read Only Memory), USB (Universal Serial Bus) memories, memory cards, FDs (Flexible Disk), hard disks, magnetic tape, cassette tapes, MOs (Magnetic Optical Disk), MDs (Mini Disk), IC (Integrated Circuit) cards (excluding memory cards), optical cards, mask ROMs, EPROMs, EEPROMs (Electronically Erasable Programmable Read-Only Memory), and so on.

Note that the sleep evaluation device 100 may further include a speaker, and the CPU 41 can then play back audio recorded by the recording module 140 when the button group 10 is manipulated.

Figure 7:
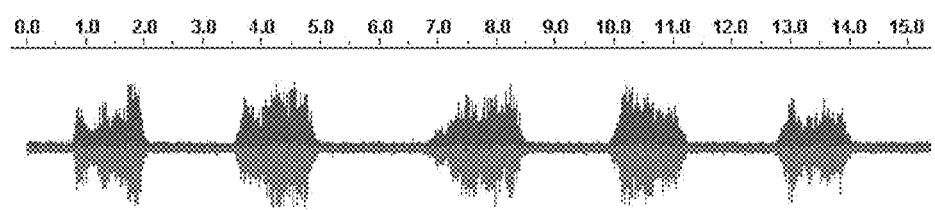
FIG. 7 is a diagram illustrating an example of an audio waveform obtained by recording snoring.

Snoring is generally synchronous with the rhythm of breathing, and occurs particularly during inhalation. FIG. 7 is a diagram illustrating an example of an audio waveform obtained by recording snoring.

As can be seen from FIG. 7, it can be said that snoring is a series of sounds occurring intermittently at essentially constant intervals. The present preferred embodiment assumes that snoring is audio in which a sounded segment greater than or equal to a set length and a silent segment greater than or equal to a set length continue in an alternating manner, where the sounded segment is defined as a segment in which the volume (sound amplitude) exceeds a given threshold and the silent segment is defined as a segment in which the volume is less than or equal to the threshold.

Figure 8:
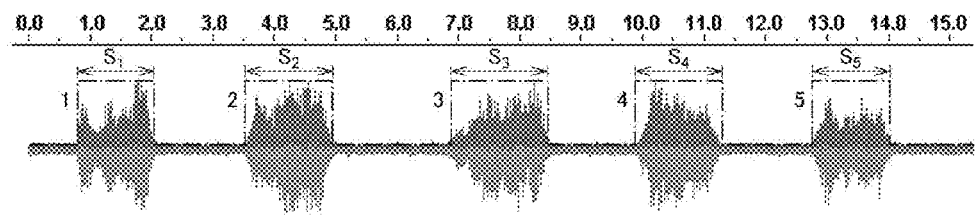
FIG. 8 is a diagram illustrating a result of binarizing the audio waveform shown in FIG. 7 based on a predetermined threshold.

Based on such definitions, a simplified audio model such as that shown in FIG. 8 can be obtained by binarizing the waveform shown in FIG. 7. FIG. 8 is a diagram illustrating a result of binarizing the audio waveform shown in FIG. 7 based on a predetermined threshold. In FIG. 8, the audio model is indicated by the dot-dash line, and the number of occurrences of sounded segments is indicated by the numbers 1, 2, and so on. Furthermore, in FIG. 8, the sounded segments are indicated by the letter S and subscript numbers indicating the corresponding occurrence number.

The absolute values of sound amplitudes are used for the modeling illustrated in FIG. 8. In other words, in the present preferred embodiment, a waveform obtained by performing full-wave rectification on the raw waveform of the inputted audio signal (that is, a waveform whose negative side has been inverted) is preferably used for snoring detection. Note that FIG. 7 and FIG. 8 show waveforms prior to the full-wave rectification.

The snoring detection unit 112 according to the present preferred embodiment obtains an index r to determine the occurrence of snoring from a snoring audio model such as that shown in FIG. 8. r is calculated according to the following Formula (1).

$$r = \frac{S}{N} = \frac{\sum_{i=1}^{n} S_i}{N} \quad (1)$$

In Formula (1), S represents the total length of all sounded segments per unit of time (for example, approximately 15 to 30 seconds). N, meanwhile, represents the number of occurrences of sounded segments per unit of time. Considering r in the context of the example shown in FIG. 8, S is the total length of time of the segments indicated by S1 to S5. N, meanwhile, is 5.

Figure 9:
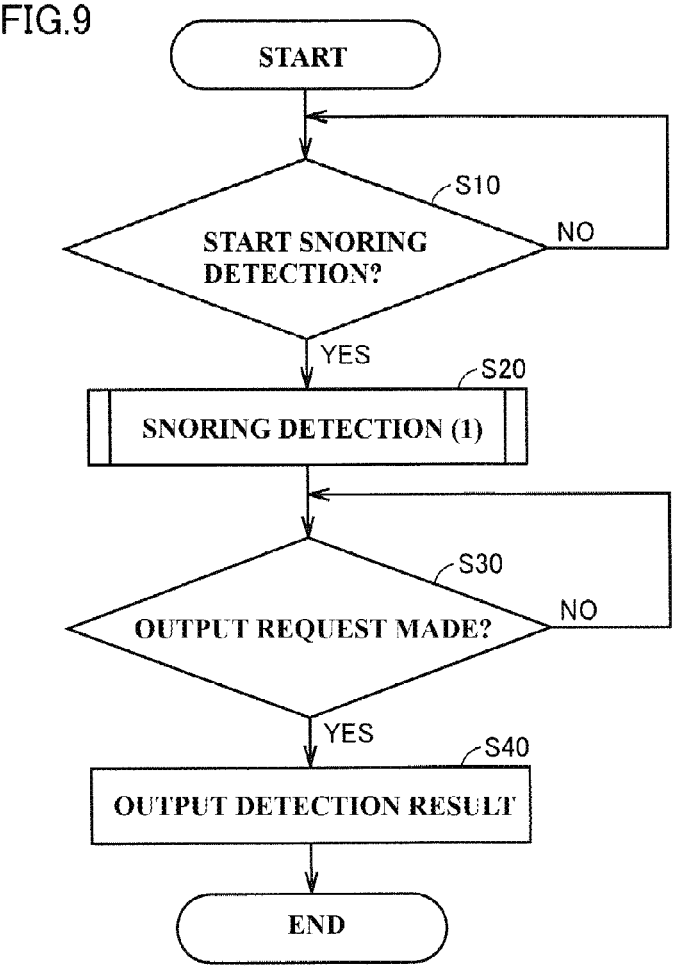
FIG. 9 is a flowchart illustrating a snoring detection process executed by a snoring detection unit.

FIG. 9 is a flowchart illustrating a snoring detection process executed by the snoring detection unit 112.

As shown in FIG. 9, first, the snoring detection unit 112 determines in step S10 whether or not a condition to start snoring detection has been met; the process advances to step S20 when it is determined that the condition has been met.

A predetermined button in the button group 10 being manipulated, a time measured by a timer 60 reaching a pre-set time to start snoring detection, the input of an instruction to start snoring detection from an external device via the communication unit 50, and so on can be given as examples of conditions to start snoring detection.

Figure 10:
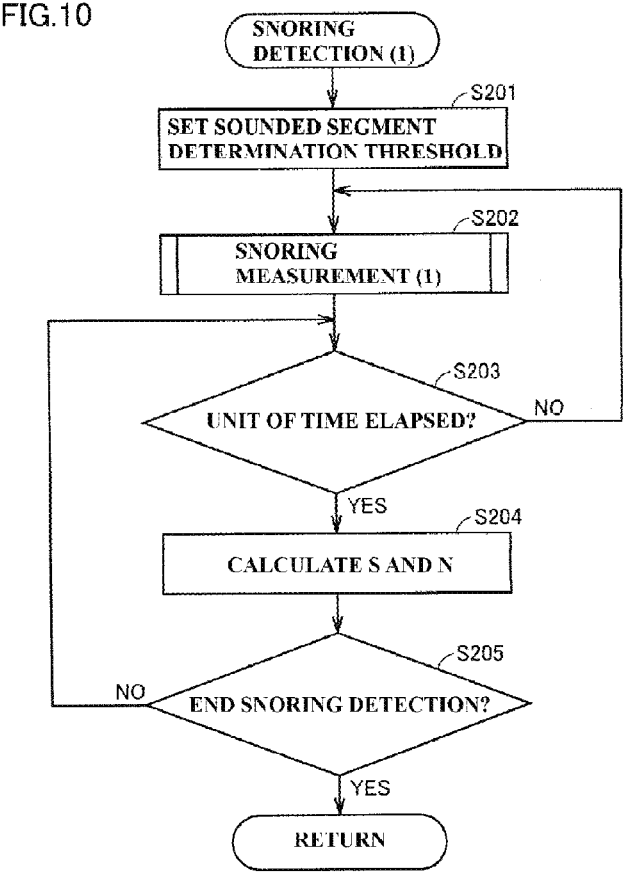
FIG. 10 is a flowchart illustrating a subroutine in the snoring detection process shown in FIG. 9.

In step S20, the snoring detection unit 112 executes a snoring detection process. The details of the process executed in step S20 will be described later with reference to FIG. 10. Note that FIG. 10 is a flowchart illustrating a subroutine in the snoring detection process executed in step S20. When the snoring detection process executed in step S20 ends, the snoring detection unit 112 advances the process to step S30.

In step S30, the snoring detection unit 112 determines whether or not there has been a request to output a detection result, and the process advances to step S40 when it is determined that such a request has been made.

In step S40, the snoring detection unit 112 outputs the detection result to the analysis processing unit 115, after which the process ends.

As shown in FIG. 10, in the snoring detection process executed in step S20, the snoring detection unit 112 first sets the sounded segment determination threshold in step S201, after which the process advances to step S202.

The setting of the sounded segment determination threshold in step S201 will now be described.

The sounded segment determination threshold is set using the audio data inputted from the audio sampling unit 111 a predetermined amount of time after the start of the snoring detection process. Note that the audio data used is data obtained by performing full-wave rectification on the raw waveform of the audio signal inputted from the audio sampling unit 111. The volume of the full-wave rectified audio data will be described hereinafter as an "AD value".

The sounded segment determination threshold is set, for example, using the maximum AD value in the predetermined amount of time (called a "max AD value" hereinafter) and the minimum AD value in the predetermined amount of time (called a "min AD value" hereinafter).

Note that depending on the combination of the max AD value and the min AD value, there are cases where snoring cannot be determined. In such a case, the snoring detection process shown in FIG. 10 is stopped (without the process advancing to step S202), and the process returns to that shown in FIG. 9. In this case, in step S40 (FIG. 9), the snoring detection unit 112 outputs a signal indicating that the detection has been stopped to the analysis processing unit 115 rather than a snoring detection result.

A case where the max AD value is less than the min AD value, the case where the max AD value is greater than or equal to the min AD value but a difference between the max AD value and the min AD value is less than a predetermined value, and so on can be given as examples of cases where snoring cannot be determined due to the combination of the max AD value and the min AD value.

A value obtained by adding the difference between the max AD value and the min AD value to the min AD value can be given as a specific example of the sounded segment determination threshold that uses the max AD value and the min AD value. This specific example will be described with reference to FIG. 11.

Figure 11:
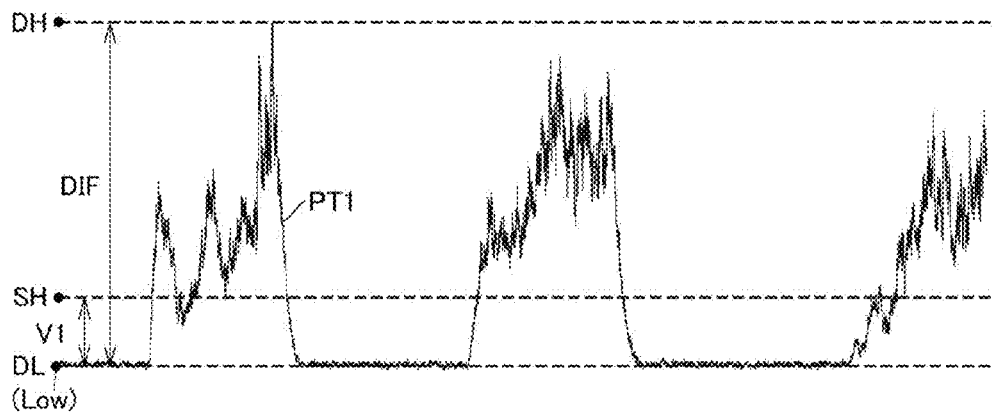
FIG. 11 is a diagram illustrating a specific example of the calculation of a sounded segment determination threshold.

The sounded segment determination threshold is indicated as a value SH in FIG. 11. When calculating the value SH, first, a difference between the max AD value ("DH" in FIG. 11) and the min AD value ("DL" in FIG. 11) is calculated. In FIG. 11, the difference is indicated by "DIF". Next, a value of a set ratio to the difference DIF (1/4, 1/5, or the like) is calculated. The "set ratio" can be set as appropriate for each environment in which the sleep evaluation device 100 is used. In FIG. 11, the value of the set ratio for the difference DIF is indicated by "V1". The min AD value plus the value V1 is then taken as the value SH, or in other words, the sounded segment determination threshold.

Returning to FIG. 10, in step S202, the snoring detection unit 112 executes a snoring measurement process, and advances the process to step S203. The snoring measurement process is a process for determining the value of the signal fSIG (1 or 0) outputted by the snoring detection unit 112. This process will be described in detail later.

In step S203, it is determined whether or not the unit of time has elapsed since the start of the snoring measurement process executed in step S202; the process returns to step S202 when it is determined that the unit of time has not elapsed, whereas the process advances to step S204 when it is determined that the unit of time has elapsed.

In step S204, S and N are calculated based on the result of the snoring measurement process executed in step S202, after which the process advances to step S205.

In step S205, it is determined whether or not a condition for ending the snoring detection has been met; the process returns to that shown in FIG. 9 when it is determined that the condition is met, whereas the process returns to step S203 when it is determined that the condition is not met.

Here, a predetermined button in the button group 10 being manipulated, an end time stored in the memory 42 in advance being reached, the input of an instruction for ending snoring detection from an external device via the communication unit 50, and so on can be given as examples of conditions for ending snoring detection.

Although the values of S and N preferably are calculated each time the unit of time elapses in the process described with reference to FIG. 10, the timing at which these values are calculated is not limited thereto; for example, the values may be calculated when data to display an analysis result, such as that shown in FIG. 21 and the like and described later, is created.

Note that in the snoring measurement process executed in step S202, the snoring detection unit 112 sets the value of fSIG to, for example, a default value of 0, and obtains the AD value for each predetermined amount of time; the value of fSIG is updated to 1 under the condition that the obtained AD value exceeds the sounded segment determination threshold for no less than a set number of consecutive times.

Note also that after the value of fSIG has been updated to 1, the snoring detection unit 112 updates the value of fSIG to 0 under the condition that the AD value is less than the sounded segment determination threshold for no less than a specific number of consecutive times.

Figure 12:
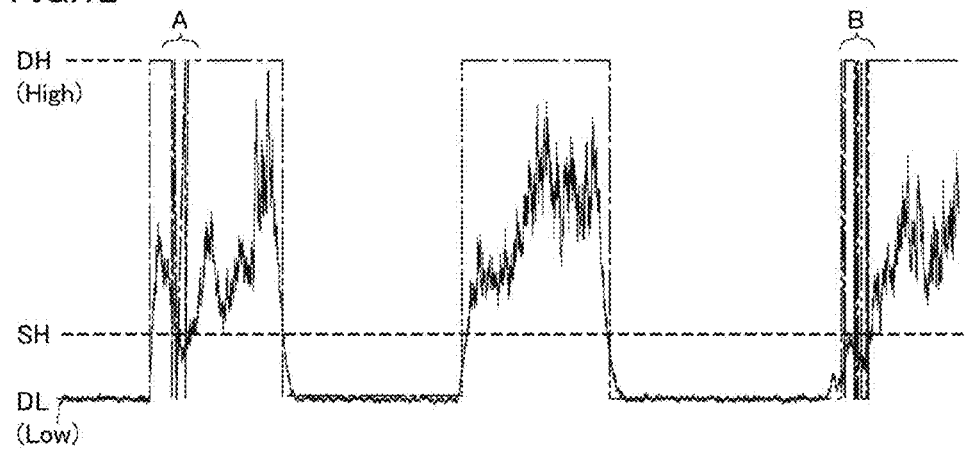
FIG. 12 is a diagram illustrating an example of audio data inputted into the snoring detection unit and a model in which the audio data has been binarized.
Figure 14:
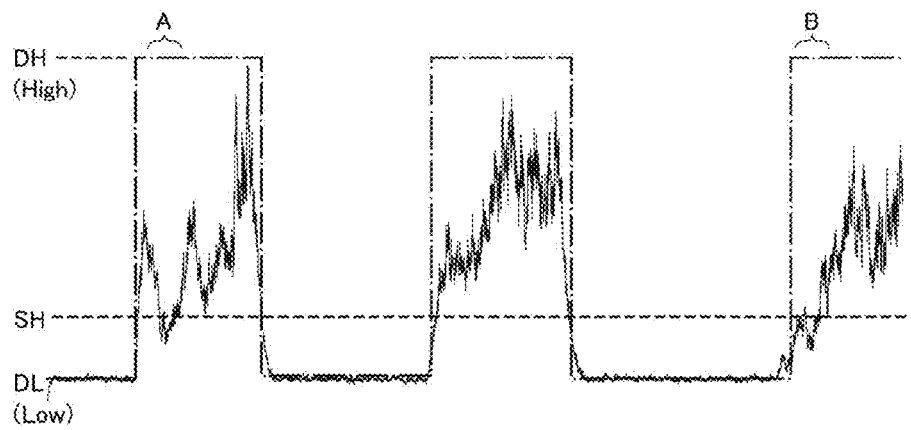
FIG. 14 is a diagram illustrating the determination of an output signal.

Setting the value of fSIG in this manner makes it possible to generate an audio model in which areas where the determination result switches in small bursts are treated as noise and removed, as shown in FIG. 14, rather than an audio model in which such small bursts are present, as shown in FIG. 12.

FIG. 12 is a diagram illustrating an example of audio data inputted into the snoring detection unit 112 and a model in which the audio data has been binarized. The audio model is indicated by the dot-dash line in FIG. 12. The audio model shown in FIG. 12 switches between High (a state of "snoring", corresponding to fSIG=1) and Low (a state of "no snoring", corresponding to fSIG=0) over a comparatively short amount of time in the areas indicated by A and B.

Figure 13:
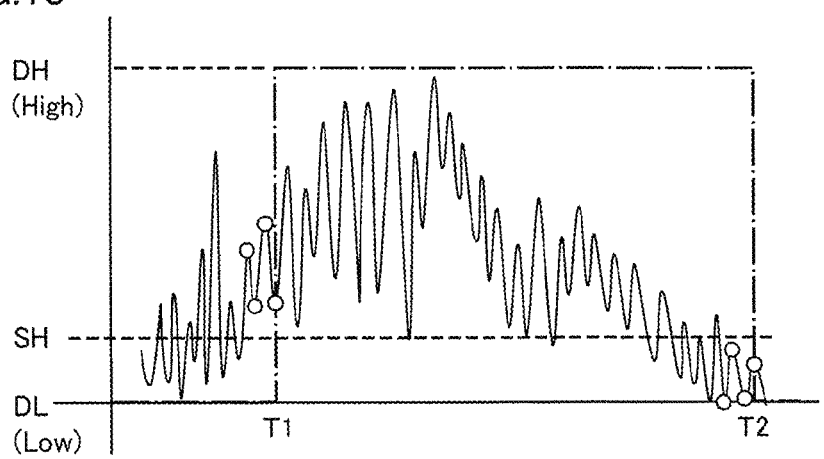
FIG. 13 is a diagram illustrating the determination of an output signal.

Meanwhile, FIG. 13 is a diagram illustrating the determination of an output signal through the snoring measurement process as described above. In FIG. 13, the volume waveform illustrated in FIG. 12 and the like has been expanded along the time axis (the horizontal axis).

The audio model indicated by the dot-dash line in FIG. 13 switches from Low to High at a time T1 and then switches from High to Low at a time T2.

In the example shown in FIG. 13, four circles are present immediately before the time T1 (that is, on the left side). These circles indicate that a value exceeding the sounded segment determination threshold (SH) has been detected four consecutive times. In this example, 4 is taken as an example of the "set number of times". The audio model shown in FIG. 13 switches from Low to High in response to a value exceeding the sounded segment determination threshold being detected four consecutive times.

Furthermore, in the example shown in FIG. 13, four circles are present immediately before the time T2. These circles indicate that a value below the sounded segment determination threshold (SH) has been detected four consecutive times. In this example, 4 is taken as an example of the "specific number of times". The audio model shown in FIG. 13 switches from High to Low in response to a value below the sounded segment determination threshold being detected four consecutive times.

Switches in the signal over a short amount of time, such as those indicated by A and B in FIG. 12, are treated as noise and removed from the audio model by switching the signal in response to values exceeding or below SH being detected a set number of consecutive times, in the manner described above; this makes it possible to generate an audio model such as that shown in FIG. 14.

The values of S and N preferably are calculated each unit of time during a detection period based on the result of the detection performed by the snoring detection unit 112 as described above. Based on this, the analysis processing unit 115 determines the value of r for each unit of time, through Formula (1).

The analysis processing unit 115 then determines a snoring level for each unit of time based on the value of r.

Note that the snoring level is set to a higher level when, for example, the value of r is greater, or in other words, when the time over which snoring occurs is longer and there is a greater number of occurrences of snoring per unit of time. Here, higher levels indicate that snoring is occurring at a higher rate.

Meanwhile, the snoring level is "0", or in other words, it is determined that there is no snoring, in the case where r is less than a specific value, the case where S exceeds a set value, or the case where N exceeds a predetermined value. In the case where S exceeds a set value, it is assumed that audio detected during the unit of time corresponding to that result is continuous audio aside from snoring, such as the sound of a siren in a vehicle passing outside, and thus it is determined that there is no snoring. In the case where N exceeds a predetermined value, it is assumed that audio detected during the unit of time corresponding to that result is continuous audio aside from snoring, such as a television or music from a stereo, and thus it is determined that there is no snoring. Note that in the present preferred embodiment, r dropping below a specific value corresponds to a case where the cumulative amount of time in which audio was obtained throughout a predetermined period is shorter than a specific amount of time, a case where the number of times audio was obtained throughout a predetermined period is less than a specific number, or the like.

Figure 21:
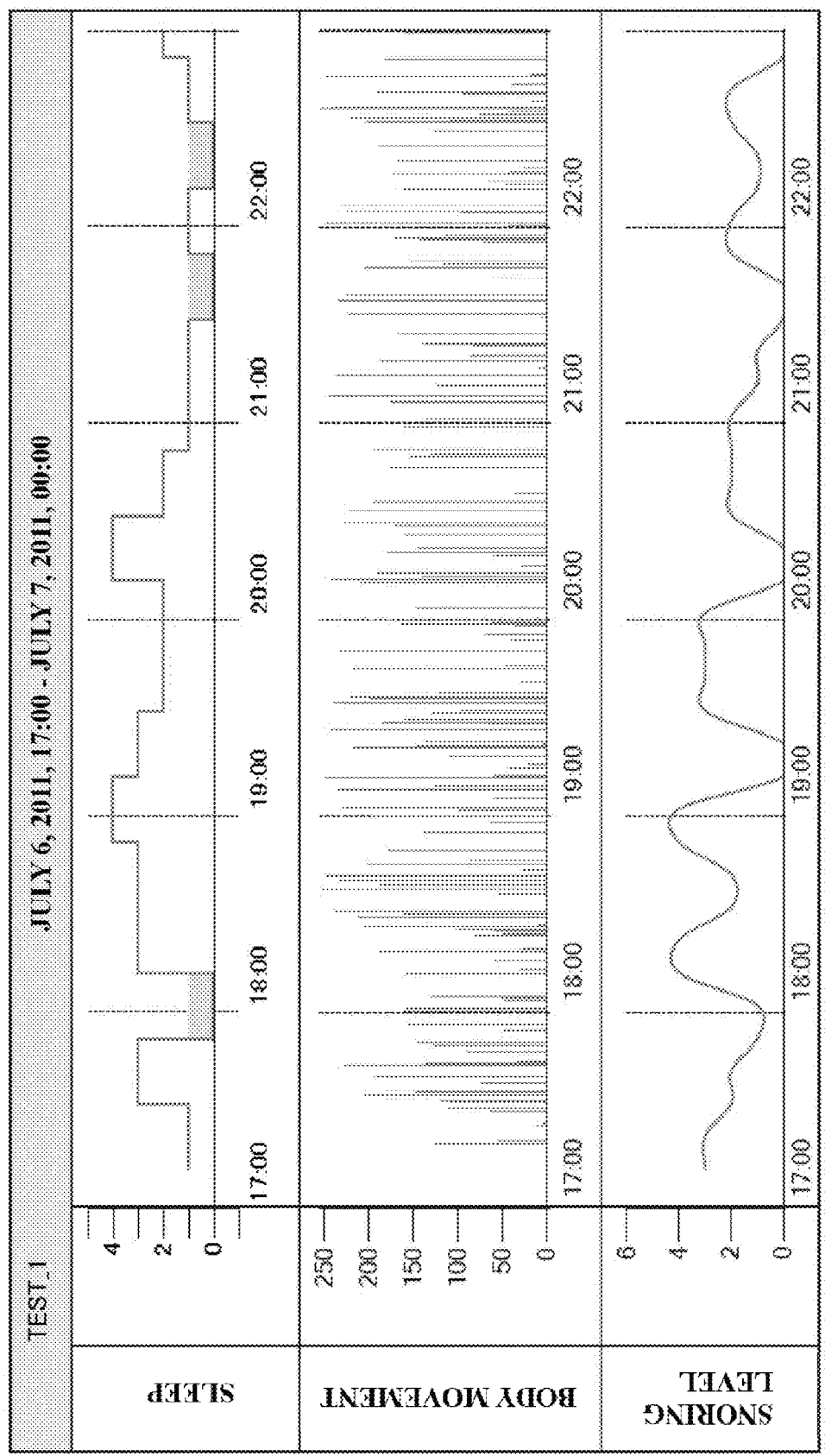
FIG. 21 is a diagram illustrating an example of a screen displaying a snoring level.

FIG. 21 is a diagram illustrating an example of a screen displaying a snoring level indicating the analysis result described above.

The screen shown in FIG. 21 displays detection results from 17:00 on Jul. 6, 2011, to 0:00 on the next day, or July 7. Note that in this example, the sleep evaluation device 100 is further configured to detect the measurement subject's depth of sleep and magnitude of body movements. In the screen shown in FIG. 21, "sleep" indicates changes in the depth of sleep, "body movement" indicates the magnitude of body movements, and "snoring level" indicates changes in the snoring level in each unit of time determined based on the value of r, the values of N and S, and so on as described above.

This screen is displayed in the display unit 20 as a detection result in step S40 based on the output request being made in step S30, for example. Note that the CPU 41 may send data to display a screen such as that shown in FIG. 21 to another device in response to a request from the other device as well.

In the "sleep" graph shown in FIG. 21, periods in which the sleep has been determined to be light (that is, in which it has been determined that the depth of sleep is less than a predetermined value) are filled in with color.

Figure 22:
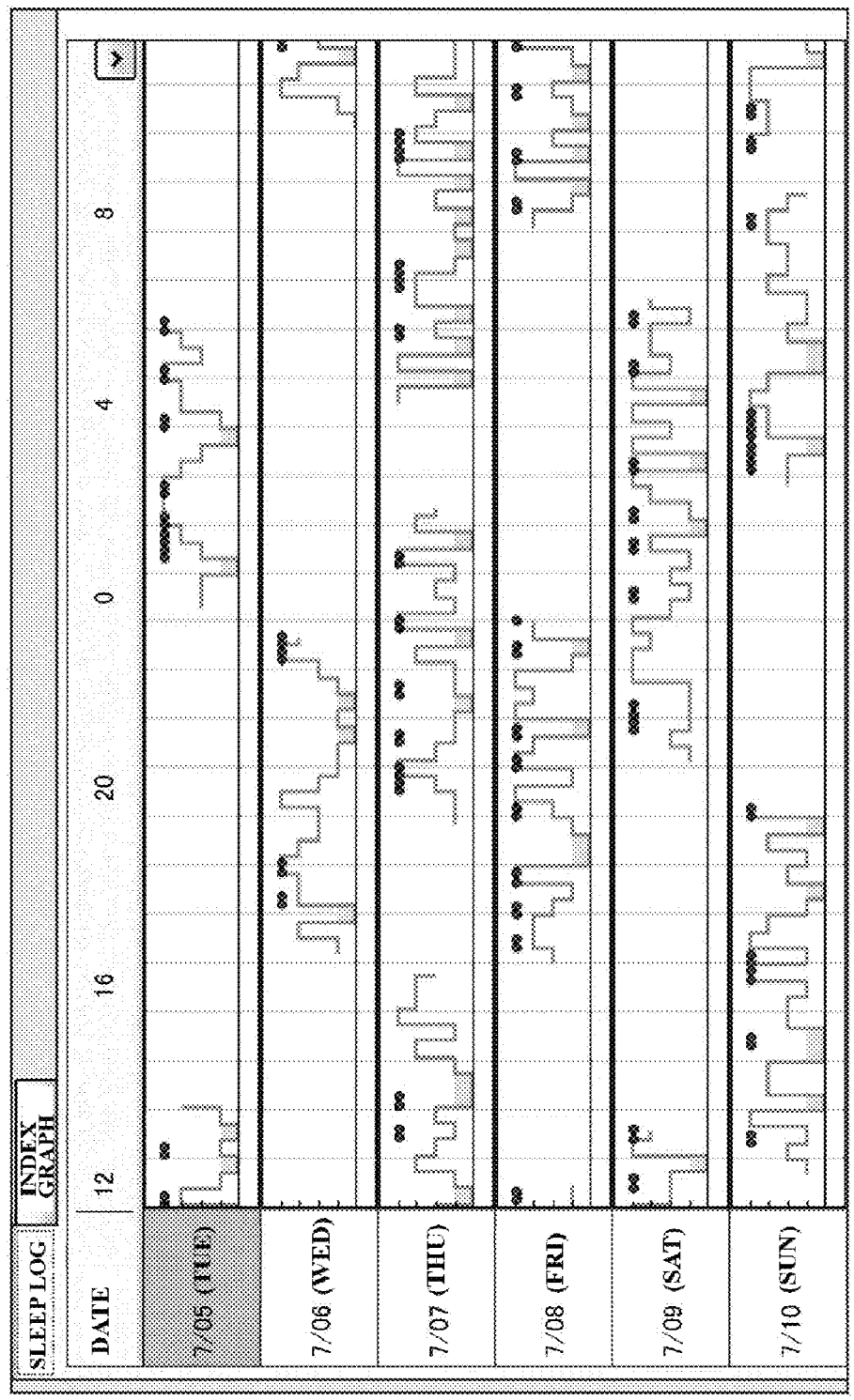
FIG. 22 is a diagram illustrating another example of a screen displaying a snoring level.

FIG. 22 is a diagram illustrating another example of a screen displaying a snoring level. The screen shown in FIG.

22 displays units of information that each correspond to 24-hour spans, from Tuesday, July 5, to Sunday, July 10.

The polygonal line graph in FIG. 22 indicates the depth of sleep. Furthermore, as in "sleep" in FIG. 21, periods in which the sleep has been determined to be light are filled in with color. Note that periods in which a polygonal line is absent correspond to periods in which sleep-related detection, such as detecting the depth of sleep, has not been carried out.

Furthermore, in FIG. 22, circles are present in various locations. These circles indicate that the snoring level determined based on the value of r, the values of N and S, and so on as described above is greater than or equal to a predetermined level (for example, a level 3).

Displaying the snoring level as shown in FIG. 21 or FIG. 22 makes it possible to objectively warn the measurement subject or the like of the occurrence of snoring.

The snoring of patients diagnosed with OSAS has the following characteristics.

1) Periods of close consecutive snores alternate with long periods of silence; and 2) unlike normal snoring, there is a trend toward sound being produced during inhaling as well.

Figure 17:
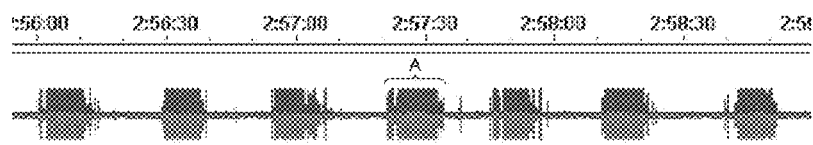
FIG. 17 is a diagram illustrating an example of a waveform obtained by recording snoring.
Figure 18:
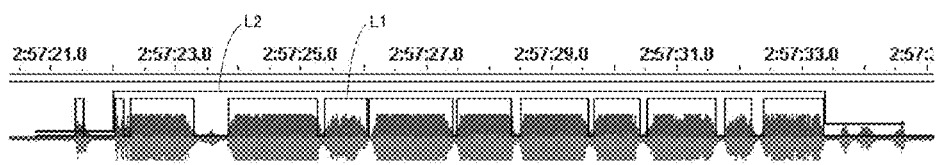
FIG. 18 is a diagram illustrating a waveform obtained by temporally enlarging a segment indicated by A in FIG. 17.

FIG. 17 is a diagram illustrating an example of a waveform obtained by recording snoring from a patient diagnosed with OSAS. FIG. 18 is a diagram illustrating a waveform obtained by temporally expanding a segment indicated by A in FIG. 17. The horizontal axis in FIG. 18 is expanded by approximately 13 to 14 times that of FIG. 17. In each diagram, the horizontal axis represents a measured time (hours:minutes:seconds). For example, "2:56:30" indicates 2 hours, 56 minutes, and 30 seconds, in the morning.

Figure 19:
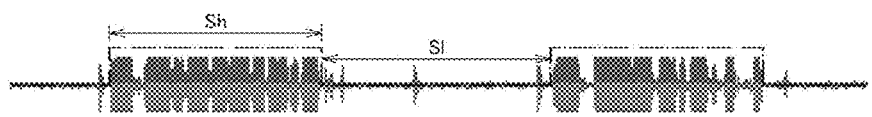
FIG. 19 is a diagram illustrating an example of an audio model generated by the SAS snoring detection unit.

In FIG. 18, the audio model generated using the sounded segment determination threshold as described above is indicated by a line L1. The SAS snoring detection unit 114 takes a series of sounded segments appearing in the line L1 as a single sound group, as indicated by a line L2, and generates the audio model. FIG. 19 is a diagram illustrating an example of the audio model generated by the SAS snoring detection unit 114. In the audio model generated by the SAS snoring detection unit 114, taking the series of sounded segments as a single sound group as indicated by the line L2 in FIG. 18 makes it possible to form sounded segments and silent segments having comparatively long spans, as indicated by Sh and Sl in FIG. 19. Accordingly, in the present preferred embodiment, an index used to identify OSAS characteristics is obtained from the results of detecting the volume of snoring.

Note that the length of each sounded segment (Sh in FIG. 19) and the length of each silent segment (Sl in FIG. 19) are examples of the stated index. In the present preferred embodiment, SAS snoring (OSAS snoring) is determined to have occurred in the case where Sl meets the condition expressed by the following Formula (2) and Sh meets the condition expressed by the following Formula (3).

$$Sl\min \leq Sl \leq Sl\max \quad (2)$$

$$Sh\min \leq Sh \leq Sh\max \quad (3)$$

In Formula (2), Slmin and Slmax represent pre-set values of Sl used for the determination. Likewise, in Formula (3), Shmin and Shmax represent pre-set values of Sh used for the determination.

Figure 15:
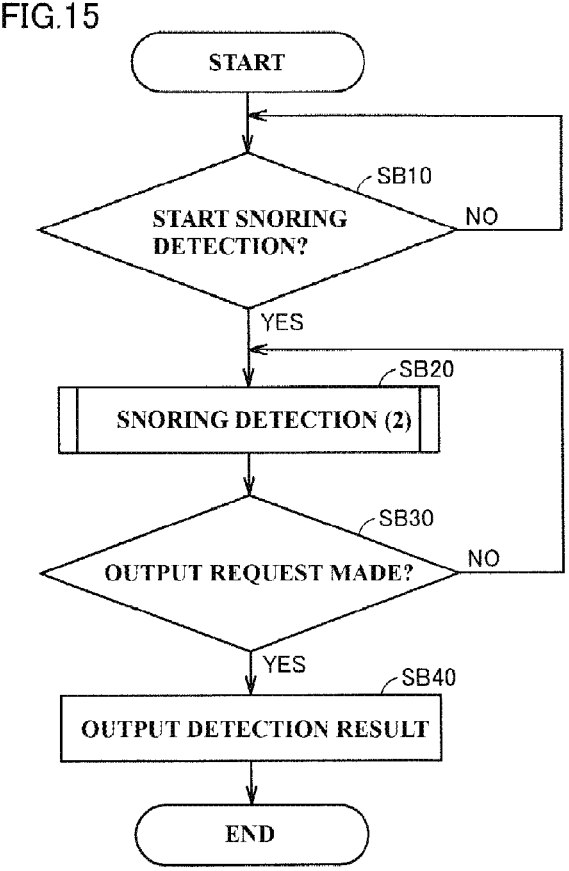
FIG. 15 is a flowchart illustrating a snoring detection process executed by an SAS snoring detection unit.

FIG. 15 is a flowchart illustrating a snoring detection process executed by the SAS snoring detection unit 114.

As shown in FIG. 15, first, the SAS snoring detection unit 114 determines in step SB10 whether or not a condition required to start snoring detection has been met; the process advances to step SB20 when it is determined that the condition has been met. A predetermined button in the button group 10 being manipulated, a time measured by a timer 60 reaching a pre-set time for starting snoring detection, the input of an instruction to start snoring detection from an external device via the communication unit 50, and so on can be given as examples of conditions required to start snoring detection.

Figure 16:
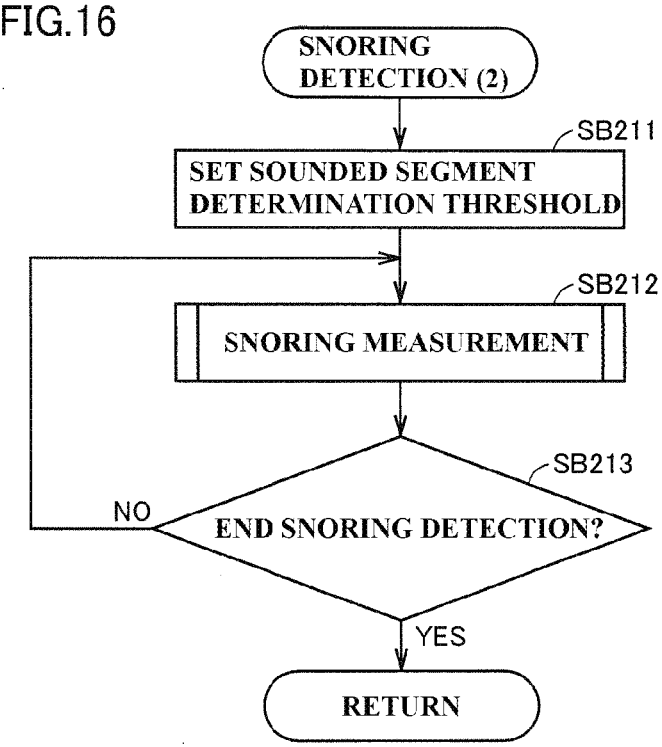
FIG. 16 is a flowchart illustrating a subroutine of the snoring detection process shown in FIG. 15.

In step SB20, the SAS snoring detection unit 114 executes a snoring detection process. The details of the process executed in step SB20 will be described later with reference to FIG. 16. Note that FIG. 16 is a flowchart illustrating a subroutine in the snoring detection process executed in step SB20. When the snoring detection process executed in step SB20 ends, the SAS snoring detection unit 114 advances the process to step SB30.

In step SB30, the SAS snoring detection unit 114 determines whether or not there has been a request to output a detection result, and the process advances to step SB40 when it is determined that such a request has been made.

In step SB40, the SAS snoring detection unit 114 outputs the detection result to the analysis processing unit 115, after which the process ends.

As shown in FIG. 16, in the snoring detection process executed in step SB20, the SAS snoring detection unit 114 first sets the sounded segment determination threshold in step SB211, after which the process advances to step SB212. The value set in step S201, for example, is used for the sounded segment determination threshold.

In step SB212, the SAS snoring detection unit 114 executes a snoring measurement process, after which the process advances to step SB213. It is then determined whether or not a condition required to end the snoring detection has been met; the process returns to that shown in FIG. 15 when it is determined that the condition is met, whereas the process returns to step SB212 when it is determined that the condition is not met. Here, a predetermined button in the button group 10 being manipulated, an end time stored in the memory 42 in advance being reached, the input of an instruction to end snoring detection from an external device via the communication unit 50, and so on can be given as examples of conditions required to end snoring detection.

In the process described above with reference to FIG. 16, the snoring measurement process continues until the condition required to end snoring detection is met.

Note that in the snoring measurement process executed in step SB212 of FIG. 16, the SAS snoring detection unit 114 preferably sets the value of an fGRP signal using a High counter and a Low counter. The SAS snoring detection unit 114 preferably then records the fGRP signal whose value has been set in this manner along with the corresponding time. As a result, the SAS snoring detection unit 114 generates an audio model as described with reference to FIG. 19 and the like.

The signal fGRP is a signal to indicate sounded segments/silent segments in the audio model in which adjacent segments of snoring are handled as a single group, as indicated by the line L2 in FIG. 18. fGRP=1 indicates a sounded segment, whereas fGRP=0 indicates a silent segment.

In the snoring measurement process, the SAS snoring detection unit 114 preferably adds 1 to the count value of the High counter when the value of fSIG has changed from 0 to 1 from when the process was previously executed to the current process execution, and adds 1 to the count value of the Low counter when the value of fSIG has changed from 1 to 0 from when the process was previously executed to the current process execution (step SC90). The SAS snoring detection unit 114 preferably then switches the result of determining whether snoring is occurring (fGRP=1/0) when the count value of the High counter or the Low counter has exceeded a predetermined threshold. In other words, the value of fGRP is switched to 1 when the value of the High counter exceeds the predetermined threshold. Likewise, the value of fGRP is switched to 0 when the value of the Low counter exceeds the predetermined threshold. As a result, an audio model in which characteristics of SAS snoring is identified, as described with reference to FIG. 19, is generated.

As described above, the fGRP signal is recorded along with the corresponding time. As a result, the SAS snoring detection unit 114 generates an audio model as described with reference to FIG. 19 and the like. In step SB40, the SAS snoring detection unit 114 calculates at least one of the indices Sh and Sl based on the stated audio model, determines whether or not SAS snoring (OSAS snoring) is occurring based on those values using Formulas (2) and (3), and outputs a result of the determination to the analysis processing unit 115.

In the preferred embodiments described above, the analysis processing unit 115 preferably calculates the snoring level based on the value of S and the value of N calculated by the snoring detection unit 112 and then causes that level to be displayed as a measurement result in the same manner as shown in FIG. 21 and FIG. 22, for example.

Note that the analysis processing unit 115 preferably also causes a time span in which it has been determined that SAS snoring is occurring based on the result of the detection performed by the SAS snoring detection unit 114 to be displayed as the measurement result. Although the measurement result is displayed along with the time of that measurement in FIG. 21 and FIG. 22, the time span in which SAS snoring occurred may be displayed by, for example, coloring the display in the areas where snoring occurred.

Furthermore, to objectively communicate the snoring that has occurred to people aside from the measurement subject or the like, the analysis processing unit 115 may record the audio obtained by the microphone 30 by causing the recording control unit 130 to operate the recording module 140 in periods in which the detection result obtained by the snoring detection unit 112 indicates a snoring level greater than or equal to a predetermined level or periods in which the detection result obtained by the SAS snoring detection unit 114 indicates that SAS snoring has occurred. The analysis processing unit 115 consecutively obtains the value of S and the value of N from the snoring detection unit 112 during snoring measurement, consecutively determines the snoring level, and then instructs the recording control unit 130 to record when the determined level has reached or exceeded the predetermined level. Furthermore, the analysis processing unit 115 consecutively obtains the detection result from the SAS snoring detection unit 114 and instructs the recording control unit 130 to record when SAS snoring occurs.

Note that the preferred embodiments disclosed above are to be understood as being in all ways exemplary and in no way limiting. The scope of the present invention is defined not by the above descriptions but by the scope of the appended claims, and all changes that fall within the same essential spirit as the scope of the claims are intended to be included therein as well.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

The invention claimed is:

1. A sleep evaluation device which analyzes a snoring level defined by a repetition of a sounded segment and a silent segment, the sleep evaluation device comprising:
    an audio sensor configured to detect the sounded segments separated by the silent segments within a predetermined period of time; and
    a processor programmed to count a cumulative time of the sounded segments within the predetermined period of time, and to count a number of occurrences of the sounded segments within the predetermined period of time; wherein
    the processor is further programmed to determine the snoring level based on a ratio of the cumulative time to the number of occurrences; and
    the processor is further programmed to determine the snoring level from among a plurality of snoring levels based on the ratio, and to display the snoring level in a display device.

2. The sleep evaluation device according to claim 1, wherein the processor is further programmed to:
    determine the snoring level in each of a plurality of predetermined periods of time; and
    determine that snoring has not occurred if the cumulative time is longer than a first predetermined time or is shorter than a second predetermined time that is shorter than the first predetermined time.

3. The sleep evaluation device according to claim 2, wherein the processor is further programmed to:
    determine the snoring level in each of the plurality of predetermined periods of time; and
    determine that snoring has not occurred if the number of occurrences is greater than or equal to a first predetermined number of times or less than a second predetermined number of times that is less than the first predetermined number of times.

4. The sleep evaluation device according to claim 1, further comprising:
    a body movement sensor configured to detect body movement in a measurement subject; and
    a display controller configured and programmed to cause the body movement detected by the body movement sensor and change over time in the snoring level determined by the determination unit to be displayed in the display device.

5. The sleep evaluation device according to claim 1, wherein:
    the processor is further programmed to determine whether or not sleep apnea syndrome snoring has occurred based on a length of the sounded segment and a length of the silent segment.

* * * * *